(12) United States Patent
Roszkowiak et al.

(10) Patent No.: US 11,246,767 B2
(45) Date of Patent: *Feb. 15, 2022

(54) EASY CHANGE PROTECTIVE UNDERWEAR

(71) Applicant: Medline Industries, Inc., Mundelein, IL (US)

(72) Inventors: Amanda Roszkowiak, Schaumburg, IL (US); Kristy Matus, Grayslake, IL (US)

(73) Assignee: Medline Industries, LP, Northfield, IL (US)

( * ) Notice: Subject to any disclaimer, the term of this patent is extended or adjusted under 35 U.S.C. 154(b) by 586 days.

This patent is subject to a terminal disclaimer.

(21) Appl. No.: 16/113,008

(22) Filed: Aug. 27, 2018

(65) Prior Publication Data

US 2020/0060890 A1 Feb. 27, 2020

(51) Int. Cl.
| | | |
|---|---|---|
| *A61F 13/496* | (2006.01) | |
| *A61F 13/49* | (2006.01) | |
| *A61F 13/15* | (2006.01) | |
| *A61F 13/474* | (2006.01) | |
| *A61F 13/514* | (2006.01) | |

(52) U.S. Cl.
CPC ...... *A61F 13/496* (2013.01); *A61F 13/49011* (2013.01); *A61F 13/15203* (2013.01); *A61F 13/474* (2013.01); *A61F 13/514* (2013.01)

(58) Field of Classification Search
CPC combination set(s) only.
See application file for complete search history.

(56) References Cited

U.S. PATENT DOCUMENTS

| | | |
|---|---|---|
| 3,424,162 A | 1/1969 | Parravicini |
| 4,122,552 A | 10/1978 | Tedford |
| 4,560,381 A | 12/1985 | Southwell |
| 4,615,695 A | 10/1986 | Cooper |
| 4,641,381 A | 2/1987 | Heran et al. |
| 4,674,135 A | 6/1987 | Greene |
| 4,745,636 A | 5/1988 | Lunt |
| 4,895,569 A | 1/1990 | Wilson et al. |

(Continued)

FOREIGN PATENT DOCUMENTS

| | | |
|---|---|---|
| CN | 202489181 U | 10/2012 |
| EP | 0405575 B1 | 9/1993 |

(Continued)

OTHER PUBLICATIONS

International Search Report and Written Opinion of the International Searching Authority, International Patent Application No. PCT/US2019/048643, Medline Industries, Inc., dated Dec. 13, 2019.

*Primary Examiner* — Michele M Kidwell
(74) *Attorney, Agent, or Firm* — Gurr Brande & Spendlove, PLLC; Robert Dan Spendlove

(57) ABSTRACT

A disposable absorbent article, including cohesive material side panels is presented in a protective underwear style to the user. The user may don the article in the same manner as a brief style undergarment or may tear the side panels and don the article in the same manner as a diaper by cohesively attaching the torn side panels. Optionally, the users may don the article in the same manner as a brief or protective underwear style article, tear at least one side panel and adjust the sizing of the side panel by cohesively reattaching the torn side panel.

17 Claims, 13 Drawing Sheets

(56) References Cited

U.S. PATENT DOCUMENTS

| | | | |
|---|---|---|---|
| 4,938,753 A | 7/1990 | Van Gompel et al. | |
| 5,085,655 A | 2/1992 | Mann et al. | |
| 5,103,501 A | 4/1992 | Meisels | |
| 5,370,634 A * | 12/1994 | Ando | A61F 13/49009 604/358 |
| 5,415,649 A | 5/1995 | Watanabe et al. | |
| 5,531,732 A | 7/1996 | Wood | |
| 5,683,373 A | 11/1997 | Darby | |
| 6,113,717 A | 9/2000 | Vogt et al. | |
| 6,182,290 B1 | 2/2001 | Morris | |
| 6,240,569 B1 | 6/2001 | Van Gompel et al. | |
| 6,247,184 B1 | 6/2001 | Watts | |
| 6,419,667 B1 | 7/2002 | Avalon et al. | |
| 6,478,786 B1 | 11/2002 | Glaug et al. | |
| 6,560,786 B2 | 5/2003 | Lipton | |
| 6,579,275 B1 * | 6/2003 | Pozniak | A61F 13/496 604/385.01 |
| 6,579,949 B1 * | 6/2003 | Hergenrother | C08F 8/42 525/342 |
| 6,682,626 B2 | 1/2004 | Mlinar et al. | |
| 6,761,711 B1 | 7/2004 | Fletcher et al. | |
| 6,849,067 B2 | 2/2005 | Fletcher et al. | |
| 6,976,978 B2 | 12/2005 | Ruman et al. | |
| 6,994,761 B2 | 2/2006 | Klemp et al. | |
| 7,150,730 B2 | 12/2006 | Hasler et al. | |
| 7,150,731 B2 | 12/2006 | Cazzato et al. | |
| 7,175,584 B2 | 2/2007 | Maxton et al. | |
| 7,318,820 B2 | 1/2008 | Avalon et al. | |
| 7,344,524 B2 | 3/2008 | Cazzato et al. | |
| 7,377,914 B2 | 5/2008 | LaVon | |
| 7,618,404 B2 | 11/2009 | LaVon et al. | |
| 7,737,324 B2 | 6/2010 | LaVon et al. | |
| 8,029,488 B2 | 10/2011 | Ashton et al. | |
| 8,043,274 B2 | 10/2011 | Mlinar et al. | |
| 8,070,738 B2 | 12/2011 | Ashton et al. | |
| 8,118,799 B2 * | 2/2012 | Datta | A61F 13/5644 604/385.11 |
| 8,545,474 B2 | 10/2013 | Schilpp et al. | |
| 8,601,665 B2 | 12/2013 | Lavon et al. | |
| 8,617,131 B2 | 12/2013 | Kline et al. | |
| 8,632,516 B2 | 1/2014 | Ashton et al. | |
| 8,663,415 B2 | 3/2014 | Thorson et al. | |
| 8,684,990 B2 | 4/2014 | Lavon | |
| 8,747,379 B2 | 6/2014 | Fletcher et al. | |
| D768,958 S | 10/2016 | Dickson | |
| D771,351 S | 11/2016 | Colon | |
| D793,029 S | 8/2017 | Dickson | |
| 9,724,251 B2 | 8/2017 | LaVon et al. | |
| 2002/0099353 A1 * | 7/2002 | Olson | A61F 13/496 604/389 |
| 2002/0111596 A1 | 8/2002 | Fletcher | |
| 2002/0165514 A1 * | 11/2002 | Datta | A61F 13/496 604/385.11 |
| 2003/0066122 A1 | 4/2003 | Niedermeyer | |
| 2003/0125702 A1 * | 7/2003 | Couture-Dorschner | A61F 13/15739 604/387 |
| 2005/0131364 A1 | 6/2005 | Sakaguchi et al. | |
| 2005/0192553 A1 * | 9/2005 | Hasler | A61F 13/5655 604/385.11 |
| 2005/0277905 A1 | 12/2005 | Pedersen et al. | |
| 2006/0068168 A1 | 3/2006 | Olson | |
| 2006/0148362 A1 | 7/2006 | Bridges | |
| 2006/0218700 A1 | 10/2006 | Uda | |
| 2006/0247595 A1 * | 11/2006 | Kawakami | A61F 13/565 604/390 |
| 2007/0049897 A1 | 3/2007 | Lavon | |
| 2007/0066951 A1 | 3/2007 | Lavon | |
| 2007/0173780 A1 | 7/2007 | LaVon | |
| 2007/0250032 A1 | 10/2007 | Andrews | |
| 2008/0065042 A1 * | 3/2008 | Wood | A61F 13/5655 604/385.201 |
| 2009/0069768 A1 | 3/2009 | Hunt | |
| 2009/0082749 A1 | 3/2009 | Scott et al. | |
| 2009/0131902 A1 | 5/2009 | Giloh | |
| 2009/0204088 A1 | 8/2009 | Stearman et al. | |
| 2009/0240226 A1 | 9/2009 | Fields et al. | |
| 2010/0125264 A1 | 5/2010 | Naylor | |
| 2010/0241096 A1 | 9/2010 | LaVon et al. | |
| 2010/0324517 A1 * | 12/2010 | Lenhult | A61F 13/84 604/385.01 |
| 2011/0071487 A1 | 3/2011 | Sabiston, Jr. | |
| 2011/0178485 A1 * | 7/2011 | LaVon | A61F 13/496 604/365 |
| 2011/0178486 A1 * | 7/2011 | LaVon | A61F 13/496 604/365 |
| 2011/0178490 A1 * | 7/2011 | LaVon | A61F 13/5655 604/385.24 |
| 2011/0202030 A1 * | 8/2011 | Ronstrom | A61F 13/68 604/385.14 |
| 2012/0046634 A1 | 2/2012 | Shields | |
| 2012/0123376 A1 | 5/2012 | Alves | |
| 2012/0152436 A1 | 6/2012 | Schneider | |
| 2013/0012907 A1 | 1/2013 | Sasayama et al. | |
| 2013/0072888 A1 | 3/2013 | Zorin | |
| 2013/0165898 A1 | 6/2013 | Rhodes et al. | |
| 2013/0230835 A1 | 9/2013 | Ellefson et al. | |
| 2013/0231625 A1 | 9/2013 | Ellefson et al. | |
| 2014/0039432 A1 | 2/2014 | Dunbar et al. | |
| 2014/0187405 A1 | 7/2014 | Volp et al. | |
| 2015/0272788 A1 * | 10/2015 | Long | A61F 13/84 604/385.11 |
| 2016/0168433 A1 * | 6/2016 | Himmelberger | C09J 153/00 428/516 |
| 2017/0035625 A1 | 2/2017 | LaVon et al. | |
| 2020/0155373 A1 * | 5/2020 | Tallman | A61F 13/622 |

FOREIGN PATENT DOCUMENTS

| | | | |
|---|---|---|---|
| EP | 0705088 B1 | 5/1999 | |
| EP | 1027874 A2 | 8/2000 | |
| EP | 1 702 598 * | 9/2006 | A61F 13/15 |
| WO | 2005016037 A1 | 2/2005 | |

* cited by examiner

EASY CHANGE PROTECTIVE UNDERWEAR

FIELD OF THE INVENTION

Embodiments of the present invention relate primarily to absorbent articles such as disposable incontinence articles, namely, disposable underwear side portions capable of modification to provide a more customized fit.

BACKGROUND OF THE INVENTION

Disposable absorbent articles are well known in the prior art and have many uses. Whether intended for infants, children, adults or the elderly, disposable pads, napkins, diapers, training pants, briefs, underwear, incontinence articles, and the like are intended to absorb and retain body discharges. As used herein, "absorbent article" will refer to all these examples.

Conventional diaper style absorbent articles typically include a front waist portion and a back waist portion which are releasably connected about the hips of the wearer during use by conventional fasteners such as adhesive tape fasteners or hook and loop type fasteners, et al. For example, the conventional fasteners typically include a pair of fasteners, located on the outermost corners of the diaper in the back waist region of the diaper and complimentary fasteners located on the front waist region.

In such a configuration, the diaper is positioned between the legs of the wearer and the fasteners are releasably attached to secure the diaper around the waist of the wearer. Such conventional diapers are easy to fasten and remove from the wearer after use. However, such conventional diapers are not provided in a pre-fastened configuration and, thus, are not configured to be pulled up or down over the hips of the wearer when the fasteners are attached.

Active adults appreciate the freedom afforded to them by incontinence absorbent articles. Such disposable articles can alleviate some of the emotional and physical discomfort of incontinence by absorbing and containing biomatter. Problems arise, however, when an active adult user must take advantage of public restrooms.

Disposable absorbent articles having the look and feel of traditional undergarments as opposed to diapers with side fastening systems are desirable by active adult users because such brief style absorbent articles may be pulled up or down over the hips of a wearer in the same manner as a traditional undergarment.

Similarly, brief style undergarments typically do not have the same bulk as traditional diaper style absorbent articles. Brief style absorbent articles often are configured to closely conform to the body of the wearer and consequently have a discreet profile under a wearer's clothing, which renders the absorbent article unnoticeable to the casual observer.

Such brief style absorbent articles are typically manufactured to include a plurality of side panels to connect the front portion left and right sides with the rear portion left and right sides. Such articles are typically manufactured in a pre-joined configuration, with side seams extending either toward the wearer (on an inside surface of the assembled article) or away from the wear (on an outside surface of the assembled article). Side seams are typically welded, bonded or adhered together and are therefore not adjustable. Further, side seams may not be designed to withstand repeated pulling up and down over a wearer's buttocks and hips without resulting in side seam failure.

Regardless of whether the side seams rupture, a wearer is presented with the problem of how to doff a used absorbent article and don an unused article in a public restroom setting without lowering clothing from about the waist and removing the clothing from about the ankles and feet.

Other brief style absorbent articles may include both side seams and secondary mechanical fasteners, for example hook and loop or releasable adhesive tape fasteners. Once a side seam is ruptured, a user relies upon a secondary fastener to maintain the absorbent article around the waist. Such fasteners, however, may have a tendency to attach to undesired locations, such as a wear's skin or clothing. Further, secondary fasteners may lack sufficient peel strength. If peel forces are too low, the act of lowering an absorbent article in a brief style condition may cause the fastener connection to rupture. Further, mechanical fasteners typically do not include stretch properties. Accordingly, when utilized, the mechanical fastener may not provide the same fit and comfort as the originally sealed side seams. Further, secondary mechanical fasteners can be a skin irritant.

The use of secondary mechanical fastener also offers a manufacturing disadvantage. Not only do they increase the materials production cost of the absorbent article, high speed operations during manufacture may damage mechanical fasteners.

To doff a used brief style absorbent article in restroom settings, a user can optionally remove shoes and lower garments and pull the absorbent article down over hips and buttocks to facilitate removal. In a public restroom setting, a user's clothing and stocking or bare feet can come into contact with a restroom floor, which can be both unpleasant and unsanitary. Still further, a user must expend considerable time doffing and donning clothing.

To save time, the user can optionally tear the absorbent article side seams and remove the soiled article, but the user is now faced with the challenge of how to don a new brief style absorbent article. To facilitate donning a new brief style absorbent article a user must still doff shoes and clothing.

A further problem relates to the size of public restroom stalls. Stalls typically include barely enough room for a person to enter a stall, let alone move sufficiently in front of a toilet bowl behind a closed door to remove clothing. In some rest room spaces the mere act of squatting and bending forward to maintain balance could result in a user's head coming in contact with the stall door.

Brief style absorbent articles often include an elasticized waist opening that when elongated expands to fit over the user's buttocks and hips. Accordingly, the act of doffing and donning brief style absorbent articles requires a user to stretch open the elastic waist opening, lift their feet and legs within an awkward, confined restroom stall space—without losing balance or falling—and inserting or withdrawing feet and legs into or from not only the elasticized waist opening, but also elasticized leg openings without touching any unpleasant or unsanitary surfaces within the stall. Such gymnastics, when performed by a person with normal agility within a confined space can be awkward at best. When performed by a person with diminished agility or flexibility of movement can lead to a risk of falls or injury.

Accordingly, there is a need for a brief style absorbent article that can be donned and doffed like brief style undergarments while also having the capability of transforming into a diaper style absorbent article that can be applied or removed without removal of a user's lower clothing from about the ankles and feet. As a result, the user can determine whether the article will be applied in a brief configuration or in a diaper configuration.

It is further contemplated that in accordance with embodiments of the present invention, a brief style absorbent article is provided with side panels which may be adjusted to improve the fit or comfort about the waist area of a user.

In embodiments of the present invention, absorbent articles require fewer components and materials to manufacture, thereby reducing manufacturing time, cost and impact on the environment.

To create multiple sizes, multiple size components are required, leading to an inefficient manufacturing process. Each size requires the manufacturer to stop the machine and change out a number of the machine's sections in order to produce the next size. After changing the machine sections, other sections need to be recalibrated in order to insure the raw material components are converted correctly. These changeovers can take anywhere between six to twelve hours depending on the machine being used by the manufacturer. This downtime reduces the amount of product the machine can produce and increases the manufacturers converting cost. Further, current adult brief machines manufactures are required to use extra steel and other materials in order to build the additional components for the additional sizes.

In accordance with embodiments disclosed herein, the machine assembling the article is set such that the side panel widths are changed from a first width to a second width in order to change over from building a first article size to a second article size. Similarly, when changing over to a third article size, the side panel widths are increased, and additionally in this embodiment, the chassis length is increased to the second chassis length as for the third article size and fourth article size. For these changes, the changeover is completed by running different programs in the machine and minimal or even zero hard tooling change over is required. By way of example, there may be no hard tool changeovers such as the replacement of cutting dies. Instead, only vacuum plate changes may be needed for the size changes in the side panel widths and length which are relatively simple replacements. In some embodiments, the vacuum plates need not even be physically replaced, the vacuum plates are sized to accommodate all sizes of side panels and depending on the size of the side panel, and vacuum ports are enabled or disable based on the size of the side panel.

BRIEF DESCRIPTION OF THE DRAWINGS

The various aspects, features and advantages of the disclosure will become more fully apparent to those having ordinary skill in the art upon careful consideration of the following Detailed Description thereof with the accompanying drawings described below.

Figure 1:
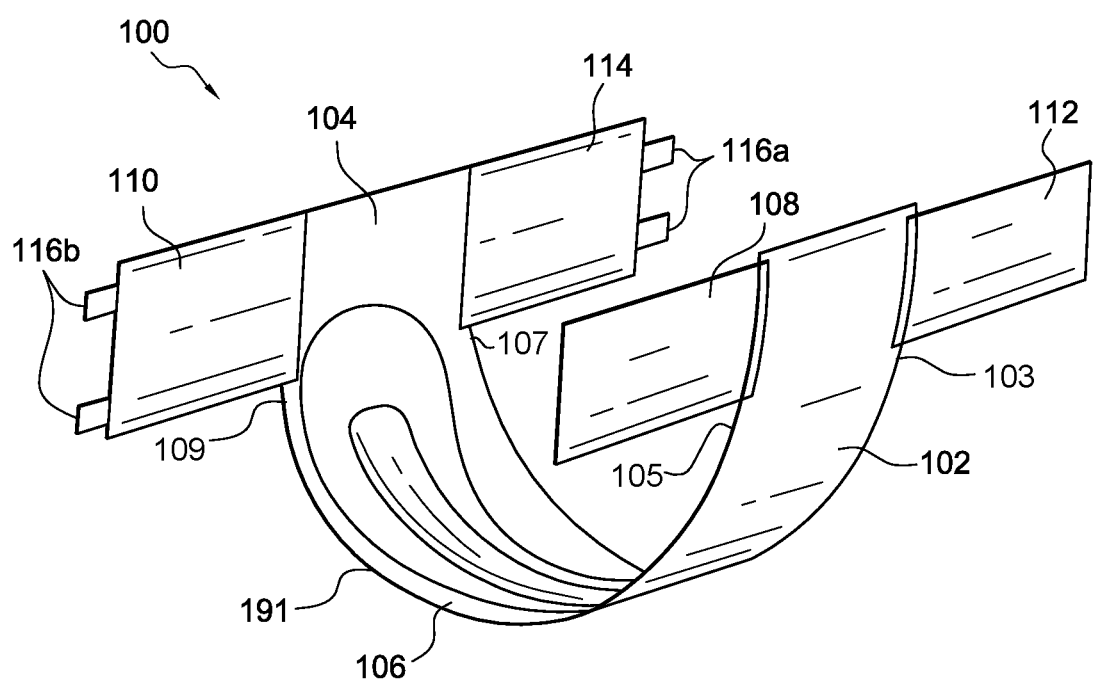
FIG. 1 is a perspective view of a diaper style absorbent article.

While embodiments of the invention are susceptible to various modifications and alternative forms, specific embodiments have been shown by way of example in the drawings and will be described in detail herein. It should be understood however, that the invention is not intended to be limited to the particular forms disclosed. Rather, the invention will cover all modifications, equivalents, and alternatives falling within the spirit and scope of the invention.

DETAILED DESCRIPTION

Embodiments of the invention are now described in detail. Referring to the drawings, like numbers indicate like parts throughout the views. As used in the description herein and throughout the claims, the following terms take the meanings explicitly associated herein, unless the context clearly indicates otherwise: the meaning of "a," "an," and "the" includes plural reference, the meaning of "in" includes "in" and "on." Relational terms such as first and second, top and bottom, left and right and the like may be used solely to distinguish one entity or action from another entity or action without necessarily requiring or implying any actual such relationship or order between such entities or actions.

As used herein, the following terms have the following meanings:

"Attach" and its derivatives refer to the joining, adhering, connecting, bonding, sewing together, or the like, of two elements. Two elements will be considered to be attached together when they are integral with one another or attached directly to one another or indirectly to one another, such as when each is directly attached to intermediate elements. "Attach" and its derivatives include permanent, releasable, or refastenable attachment. In addition, the attachment can be completed either during the manufacturing process or by the end user.

"Bond" and its derivatives refer to the joining, adhering, connecting, attaching, sewing together, or the like, of two elements. Two elements will be considered to be bonded together when they are bonded directly to one another or indirectly to one another, such as when each is directly bonded to intermediate elements. "Bond" and its derivatives include permanent, releasable, or refastenable bonding.

"Cohesive material" refers to a material which demonstrates surface interaction (in terms of connection of one surface to another) when applied to a specially selected material. Cohesive material will fasten or form a connection primarily to itself or to similarly structured materials. Generally, such materials are substantially non-tacky (such as to skin) at room temperature even under some pressure. For purposes of the present specification, the term cohesive will include materials which are sometimes referred to as "selectively adhesive" or "selective adhesive" materials. Materials which are designed to receive (i.e. allow the surface interaction) with a particular cohesive material, but which themselves will not connect with any other materials (or itself) are still considered "cohesive materials" within the meaning of this specification when they act as the target surface for a specific cohesive engaging material. Because the cohesive material will connect or fasten to selective materials and not to other materials generally, this allows for disposition of cohesive polymers onto multiple surfaces of a target material. By contrast, most mechanical fastening systems (such as hook and loop systems) require that the complimentary components be mated in only one relationship to work properly. Cohesive materials may be a bandage type cohesive material or other appropriate cohesive materials.

"Connect" and its derivatives refer to the joining, adhering, bonding, attaching, sewing together, or the like, of two elements. Two elements will be considered to be connected together when they are connected directly to one another or indirectly to one another, such as when each is directly connected to intermediate elements. "Connect" and its derivatives include permanent, releasable, or refastenable connection. In addition, the connecting can be completed either during the manufacturing process or by the end user.

"Integral" is used to refer to various portions of a single unitary element rather than separate structures bonded to or placed with or placed near one another.

"Extensible" refers to materials which elongate or increase in at least one dimension when subject to an external pulling force.

"Elastic," "elasticized" and "elasticity" mean that property of a material or composite by virtue of which it tends to recover its original size and shape after removal of a force causing a deformation.

"Elastomeric" refers to a material or composite which can be elongated by a percent of its relaxed length and which will recover, upon release of the applied force by a percent of its elongation. In certain embodiments, an elastomeric material or composite may be capable of being elongated by at least 100 percent, in further embodiments by at least 300 percent of its relaxed length. Embodiments of the elastic material or composite may recover, upon release of an applied force, at least 50 percent of its elongation.

As used herein the term "refastenable" refers to the attachment of two or more elements or portions of elements together in a manner in which they can be separated and re-attached successively without substantial degradation of fastener performance or damage to surrounding components of the article which would impair its continued use. It will be appreciated that a refastenable component need not have an infinite life span, but it is sufficient that the components attached in a refastenable manner can be separated and re-attached successively several times over the typical use life span of the article. It will also be appreciated that the aggressiveness of actual fastening or tack may be reduced significantly from fastening to refastening in absolute terms, but that such reduction is not substantial degradation of fastener performance if the resulting refastened strength is sufficient for its purpose of use in a disposable absorbent article.

"Stretchable" or "elastic" are intended to be interchangeable and refer to materials which are extensible and which also return to substantially their original dimensions when the external pulling force is removed. It will be appreciated that the terms stretchable and elastic include the term extensible as each term is used herein.

These terms may be defined with additional language elsewhere in the specification.

Absorbent articles as described herein generally include a moisture-pervious inner layer, an absorbent layer, and a liquid-impervious outer layer. Although the remainder of the description will be specifically directed to adult incontinence articles, including disposable briefs and underwear (whether intended for men or women), it is understood that the embodiments may also be implemented on other absorbent articles, whether intended for infants, children, adults or the elderly. As would be understood by one of ordinary skill in the art, such non-limiting examples include: diapers, training pants, and the like which are intended to absorb and retain body discharges.

It should be observed that the embodiments reside primarily in the combinations of assembly components and method steps for using various embodiments of the absorbent articles disclosed herein. Accordingly, the assembly components and the method steps have been represented (where appropriate) by conventional symbols in the drawings, showing only those specific details that are pertinent to understanding the embodiments of the present invention so as not to obscure the disclosure with details that will be readily apparent to those of ordinary skill in the art having the benefit of the description herein.

FIG. 1 illustrates a disposable diaper 100 configuration of an absorbent article, including a chassis 191 having a front portion 102, a rear portion 104, a crotch portion 106 extending longitudinally between the front portion 102 and the rear portion 104 wherein at least a portion of the chassis 191 is configured to absorb body discharges. Front portion 102 comprises a first longitudinal side edge 103 and a second longitudinal side edge, and rear portion 105 comprises a first longitudinal side edge 107 and a second longitudinal side edge 109. Extending laterally from the front and rear portion left and right sides are side panels 108, 110, 112, 114. Complementary mechanical fastening elements 116 a, 116 b may be attached to one or more of the side panels 108, 110, 112, 114. In the illustrative embodiment, left side complementary fasteners 116 a are attached to left side rear side panel 114, and right side complementary fasteners 116 b are attached to the right side rear side panel 110.

In use, the diaper 100 chassis 191 is inserted between the wearer's legs with the diaper rear portion 104 covering at least a portion of the wear's buttock region and the diaper front portion 102 covering at least a portion of the wearer's front pelvic region. To secure a diaper 100 around a wearer's waist and leg regions, left side front and rear side panels 112, 114 are joined. This joining may be accomplished by attachment of the left side complementary fasteners 116 a to an outside surface of left side front side panel 112 and attachment of the right side complementary fasteners 116 b to an outside surface of right side front side panel 108. To remove a soiled diaper 100, clothing is lowered from about the waist and gathered about the ankles, the diaper fasteners 116 a, 116 b are released and the diaper 100 is removed from between the wearer's legs. Optionally, the diaper fasteners 116 a, 116 b can be released and refastened, allowing the wearer or caregiver to inspect the diaper 100 interior and then refasten the diaper 100 if the diaper 100 remains in a use condition.

Figure 2:
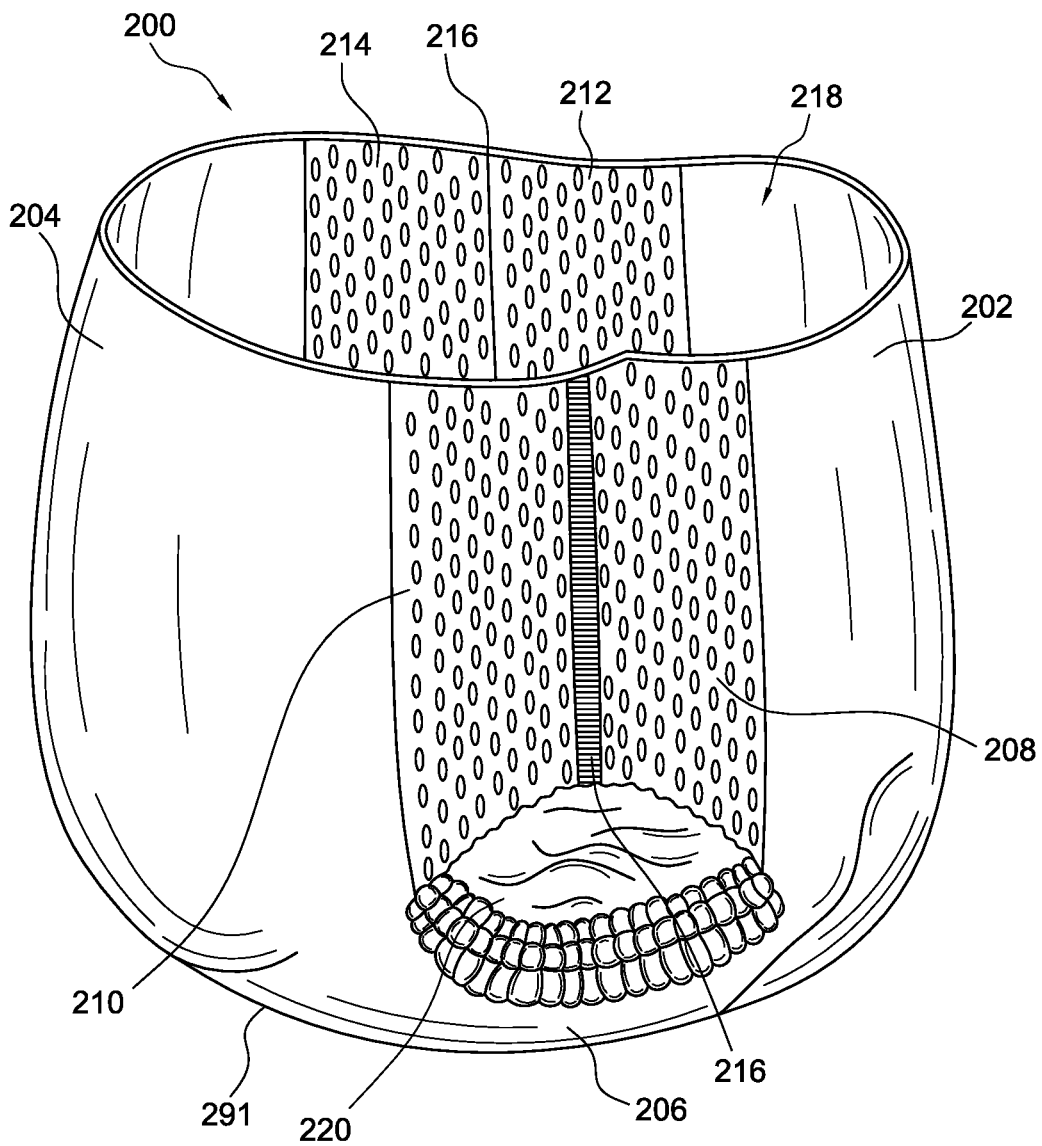
FIG. 2 is a side view of brief style absorbent article illustrating side seams.
Figure 3:
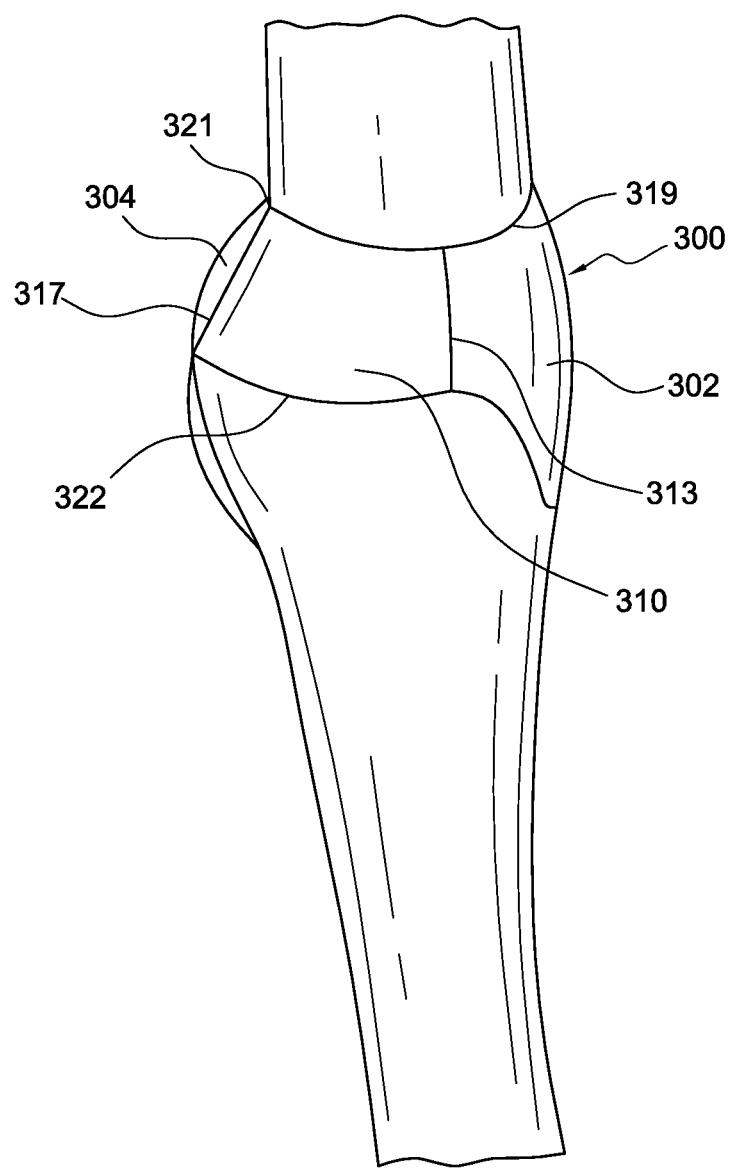
FIG. 3 is a side view of an embodiment of an absorbent article in a closed, use condition.
Figure 4:
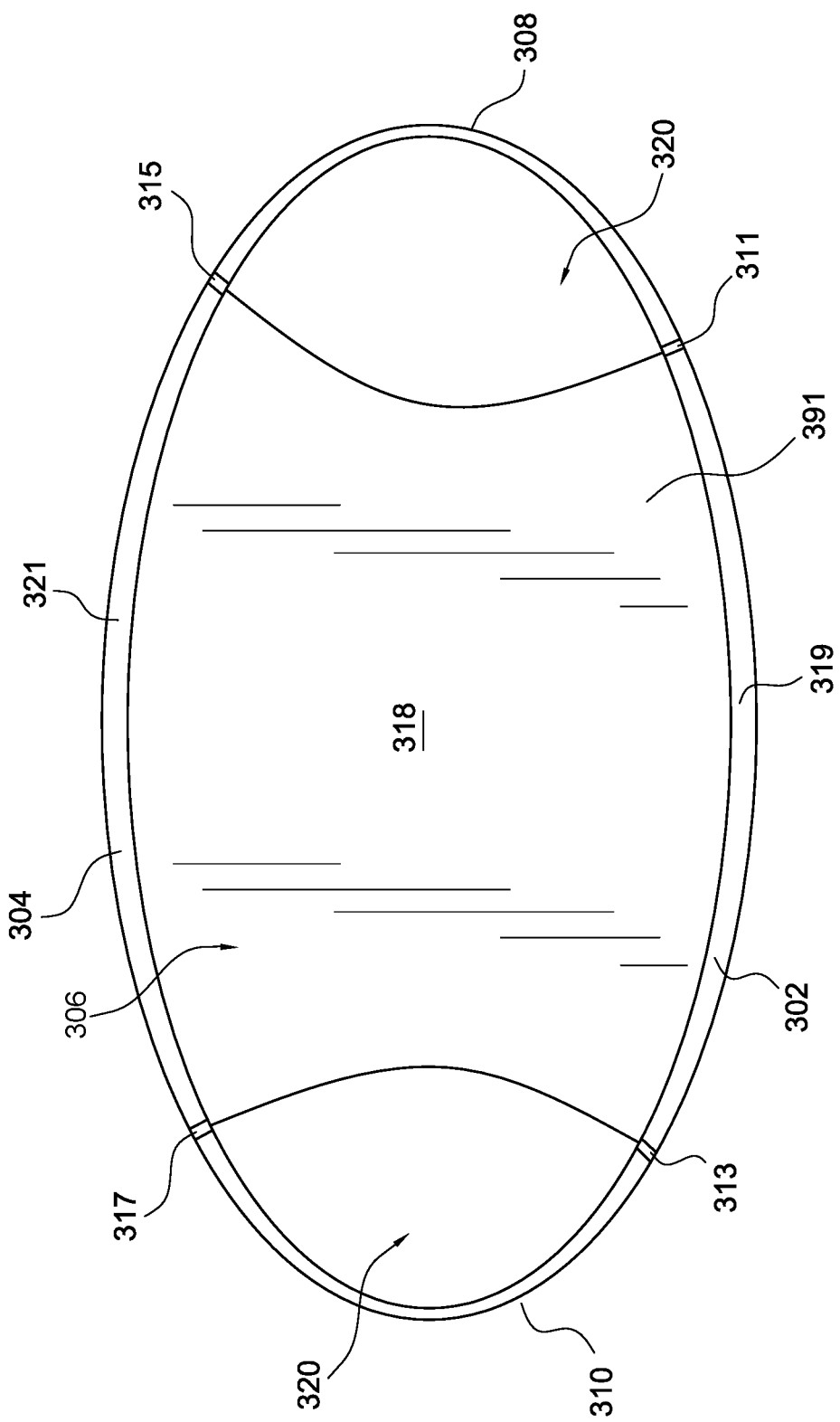
FIG. 4 is a top view of the absorbent article FIG. 3 in a closed, use condition.
Figure 5:
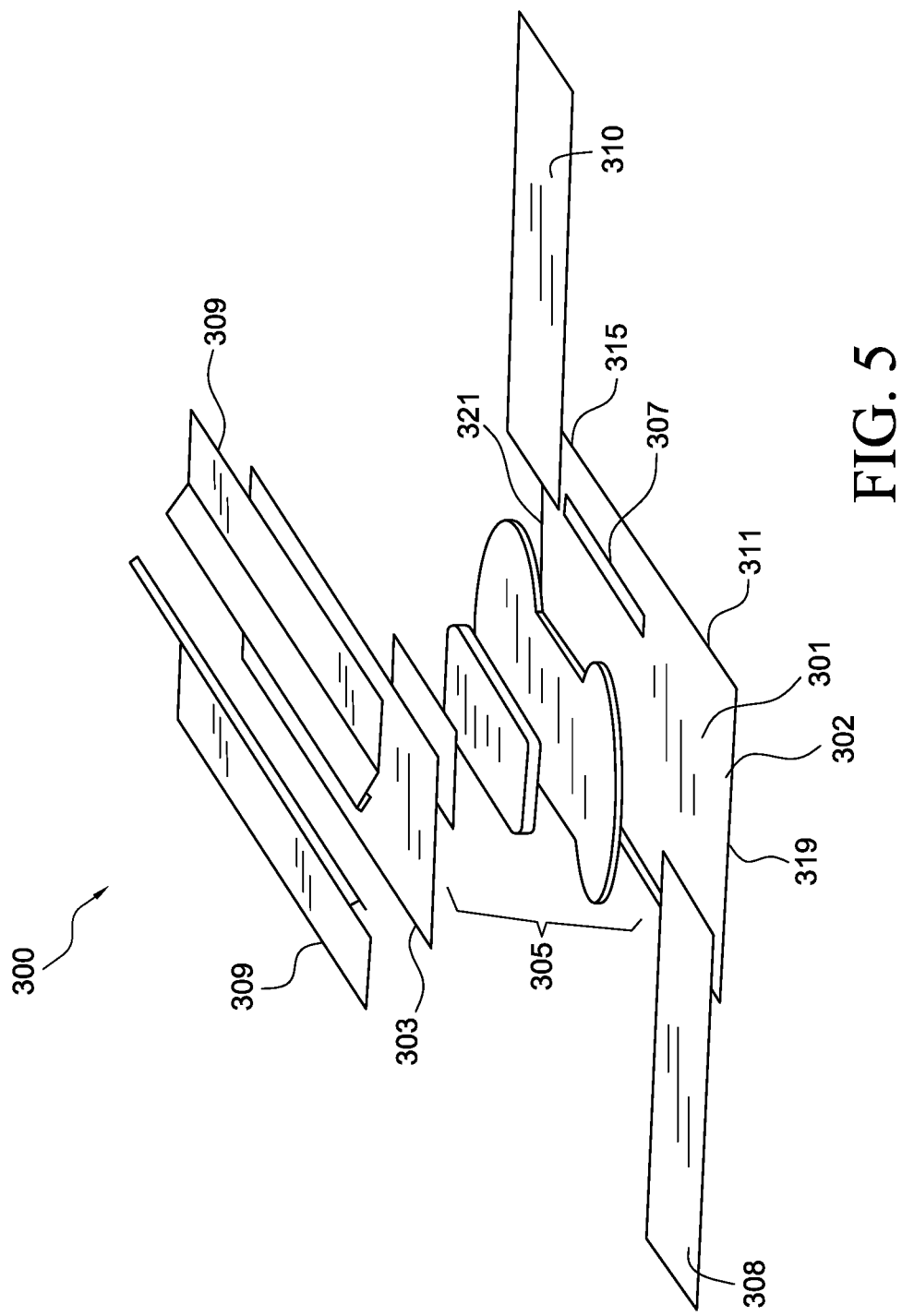
FIG. 5 is an exploded view of the absorbent article FIG. 3 in an open, flat condition.
Figure 6:
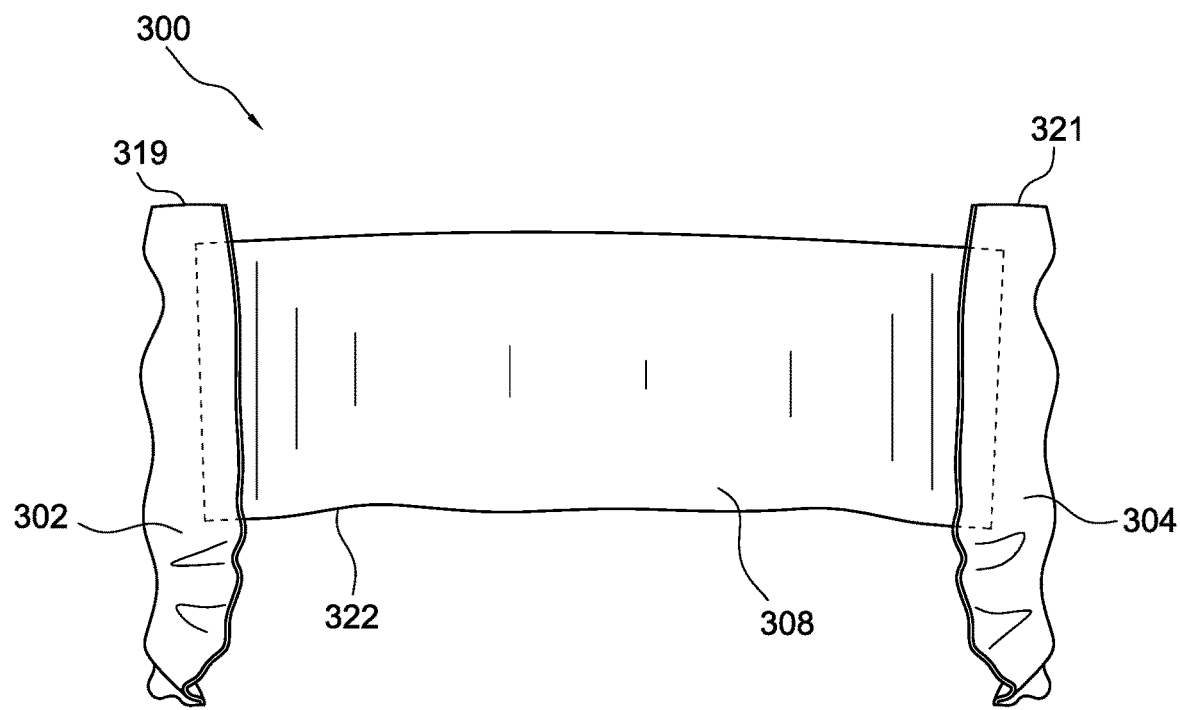
FIG. 6 is a plan view of a side panel of the absorbent article FIG. 3 in a closed, use condition.
Figure 6A:
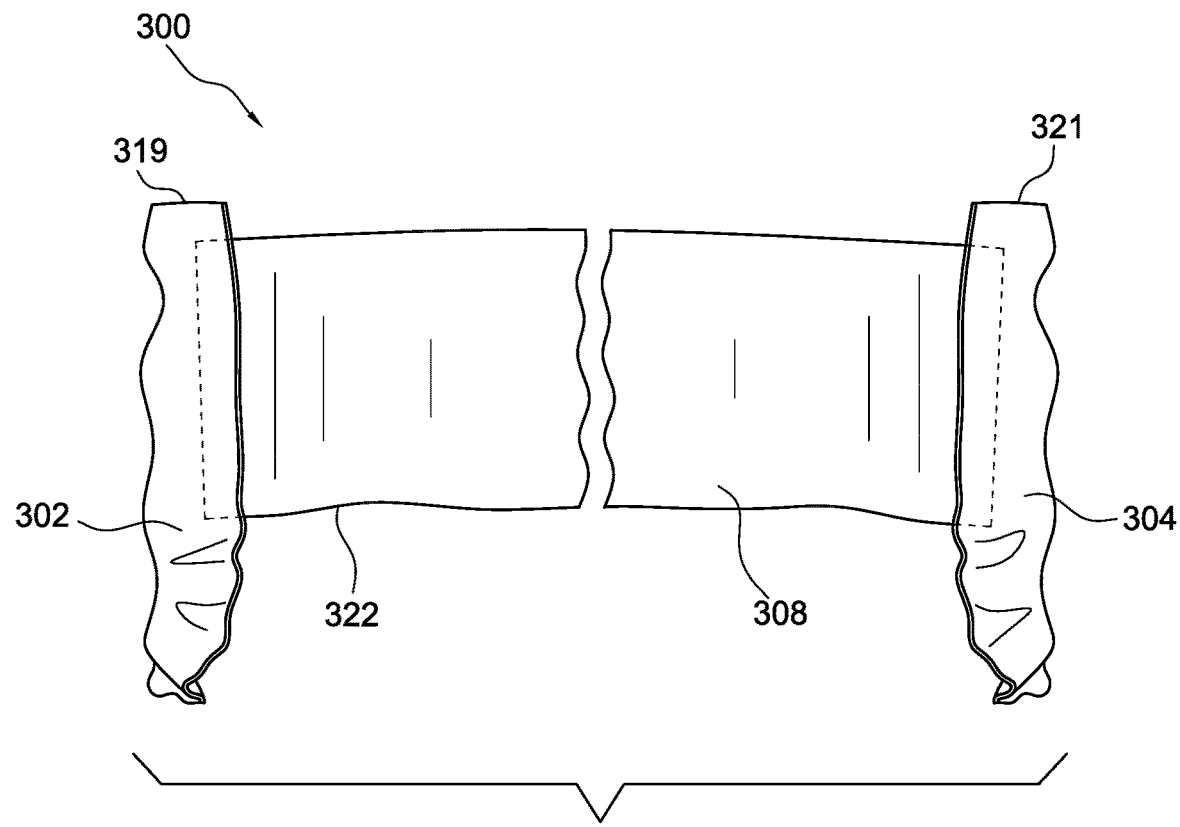
FIG. 6A is a plan view of the absorbent article of FIG. 6 after separating the side panel into two segments.

FIG. 2 illustrates a brief style disposable absorbent article 200, sometimes referred to as a training pant, pull-up, pull-on style diaper, etc. Such examples typically include a chassis 291 having front portion 202, a rear portion 204, a crotch portion 206 extending longitudinally between the front portion 202 and the rear portion 204 wherein at least a portion of the chassis 291 is configured to absorb body discharges. Extending laterally from the front and rear portions 202, 204 left and right sides are left side panels 212, 214 and right side panels 208, 210. These panels may be formed separately and joined by a seam 216 or integrally formed. Additionally, the panels may be separately formed and attached to the front and rear portions 202, 204 of the chassis 291, or they may be integrally formed with one or more layers of the front and rear portions.

Whereas diaper 100 side panels 108, 112, 112, 114 are joined by complementary fasteners 116 a, 116 b, brief style absorbent article left front and rear side panels 212, 214 and right front and rear side panels 208, 210 may be welded, bonded or adhered together with seam 216 raw edges facing toward a wearer on an inside surface of the article or facing away from a wearer on an outside surface of the article. Once bonded, a waist opening 218 and leg openings 220 are formed.

In use, a user enters the brief style absorbent article 200 using the same techniques used to don cloth undergarments. To remove the brief style absorbent article 200, shoes are removed, clothing is lowered from about the waist and completely removed from about the ankles and feet, followed by lowering and removing the brief style absorbent article 200 in the same manner as cloth undergarments. Optionally, instead of lowering and removing the brief style absorbent article 200 a wearer or caregiver can rupture the side seams 216 or tear the side panel material, rendering the article 200 unsuitable for reuse. In some examples, the brief style absorbent article 200 may include secondary mechanical fasteners (not shown), such as hook and loop fasteners, buttons, tabs, slots, hook and eye, and other mechanical fasteners to allow the article to be used following side seam rupture. The ruptured seams, however, can cause skin abrasion and secondary fasteners can become undesirably adhered to skin, hair, clothing or other undesirable surfaces. Further, mechanical fasteners lack elasticity and add bulk to the article profile.

FIGS. 3-6 illustrate embodiments of disposable absorbent articles, more particularly, a absorbent article 300. As shown particularly in FIG. 5, the absorbent article 300 generally includes several layers: a liquid-impervious outer layer 301, an inner layer 303 substantially co-extensive with the outer layer 301 and one or more absorbent and/or distribution layers 305 interposed between the outer layer 301 and inner layer 303.

The inner layer 303 may be composed of a moisture-pervious fabric suitable to allow body discharges to pass through the inner layer 303 and be absorbed by the absorbent and/or distribution layer 305. Non-limiting examples of materials suitable to form the inner layer 303 include polypropylene, polyethylene, polyester, materials having hydrophobic properties, combinations thereof and/or the like. Additionally, the inner layer 303 can be treated with a hydrophilic finish to improve passage of fluids through to diaper layers beneath the inner layer 303. Non-limiting examples of suitable hydrophilic finishes include stearic acid, melamine-based chemicals, fluorocarbon chemicals, and silicon based chemicals.

The outer layer 301, which faces away from the wearer, is composed of a liquid-impervious fabric. Accordingly, the outer layer 301 may be made of any material suitable to minimize or prevent biomatter from escaping the absorbent article 300. Non-limiting examples of suitable materials for the outer layer 301 include polyethylene or other polymer materials and may be breathable.

In some embodiments, the absorbent article 300 can include a set of leak guards 307 and/or a set of leg cuffs 309.

Embodiments of the absorbent article include a chassis 391 having a front portion 302, a rear portion 304, a crotch portion 306 connected there between, and a plurality of laterally extending side panels corresponding with a wearer's hip region. The front portion 302 defines a pair of laterally opposed side edges 311, 313 and a longitudinally opposed waist edge 319. The rear portion 304 defines a pair of laterally opposed side edges 315, 317 and longitudinally opposed waist edge 321. The front portion 302 and the rear portion 304 encompass a single layer of material, or may be constructed from a laminate material, elastomeric laminates, films, etc. or may have applied or attached elastic fibers. The plurality of side panels extend laterally outward from and between each opposed side edge 311, 313, 315, 317 of the front and rear portions 302, 304.

In certain embodiments, the side panels 308, 310 may be attached to the front and rear portions 302, 304 by welding, bonding, adhesive, or sewing, or other suitable techniques. In some embodiments, the side panels 308, 310 may be attached in between the outer and inner layers 301, 303. In other embodiments, the side panels 308, 310 may be attached to the outer layer 301. In a still further embodiment, the side panels 308, 310 may be attached to the inner layer 303. In a further embodiment, the side panels 308, 310 may be attached to both the outer and inner layers 301, 303.

Left and right leg openings 320 are defined by bottom edges 322 of the side panels 308, 310 and the longitudinal edge portions of the front, rear portions 311, 315, 313, 317. In accordance with the embodiments of FIGS. 3-6, the plurality of side panels includes two side panels. The first side panel 308 which when joined to the left side front portion longitudinal edge 311 and left side rear portion longitudinal edge 315 forms a left leg opening 320. The second side panel 310, which when joined to the right side front portion longitudinal edge 313 and the right side rear portion longitudinal edge 317 forms a right leg opening 320. In this manner, the respective waist regions of the front and rear portions 319, 321, together with the side portions 308, 310 form a complete waist opening 318.

In accordance with certain embodiments, including at least the embodiment illustrated in FIGS. 3-6, the side panels 308, 310 may be constructed from cohesive material. Cohesive material may be extensible and elastomeric. In accordance with embodiments, the cohesive material may expand laterally. In addition, the cohesive material may be such that after extension, the cohesive material will contract to its original lateral dimension, or in alternative embodiments to within 50% of its original lateral dimension. Owing to the expansion and contraction properties, the cohesive side panels 308, 310 will provide consistent support and maintain compression around the waist and/or legs of the user. Accordingly, the act of pulling the absorbent article 300 and the corresponding extension of the waist band opening 318 and side panels 308, 310 up over the wearer's buttocks and hips followed by releasing the waist band opening 318 (and side panels 308, 310) will not substantially detract from the intended fit of the absorbent article 300 around a user's waist region.

A wide variety of cohesive materials may be used to form the cohesive refastenable features discussed herein. For example, the side portions of the absorbent article may be formed, at least in part from cohesive material. Embodiments of the side portions will demonstrate high resistance to shear forces in use, but significantly less resistance to peel forces in use. For example, the cohesive materials may be chosen to demonstrate resistance to shear forces greater than 10 N, preferably greater than 30 N. Similarly the resistance to peel forces might range from about 0.5 N to about 25 N, or could range from about 0.5 N to about 15 N, and could range from about 0.7 N to about 10 N. The cohesive materials may be chosen such that the cohesive material may be refastened at least three or more times before product disposal.

Figure 9:
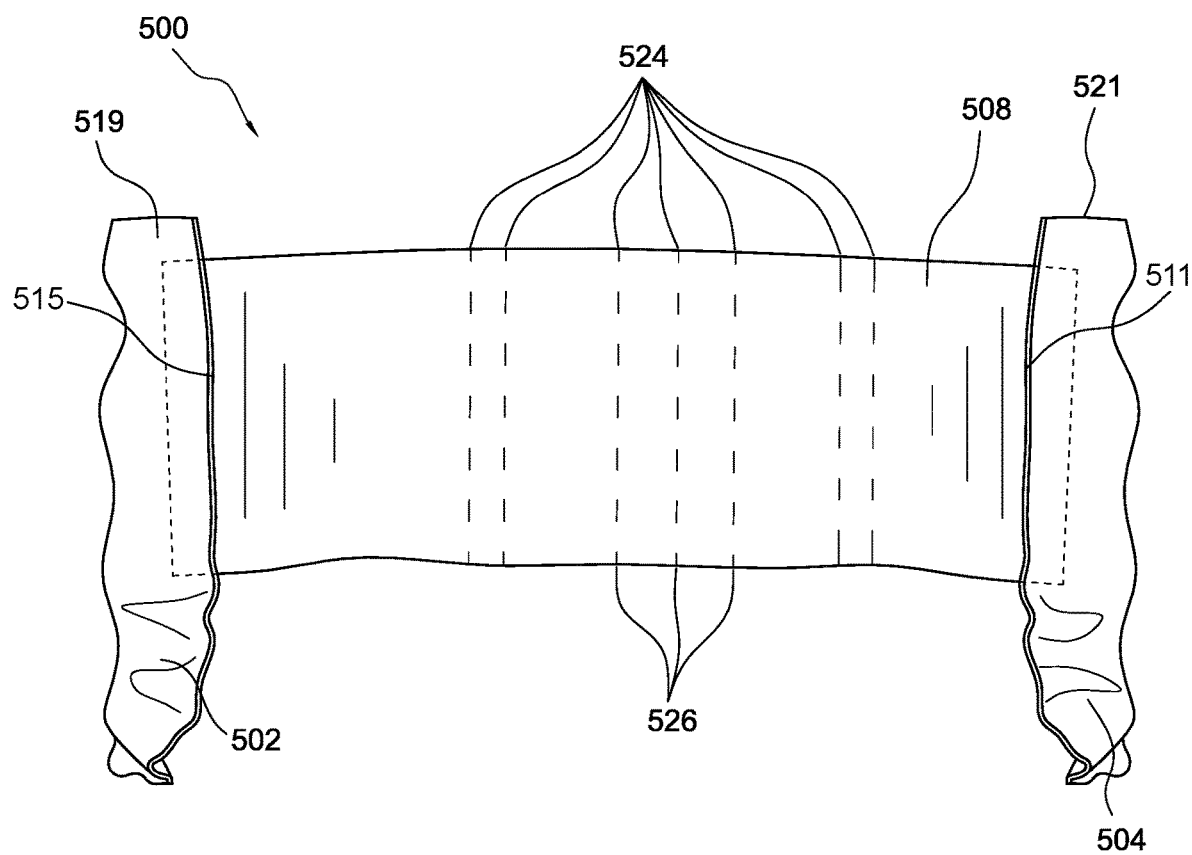
FIG. 9 is a plan view of the side panel of the absorbent article FIG. 8 in a closed, use condition.
Figure 10:
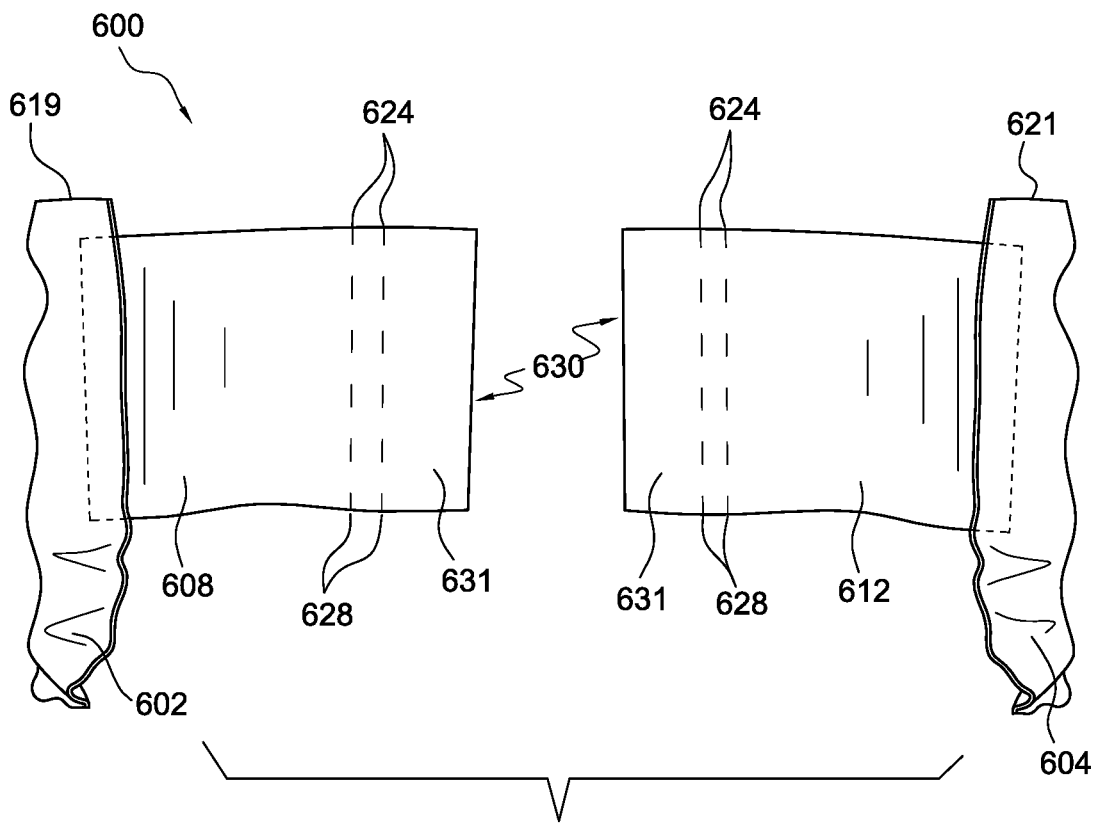
FIG. 10 is a plan view of the absorbent article of FIGS. 8-9 after separating the side panel into two segments.
Figure 11:
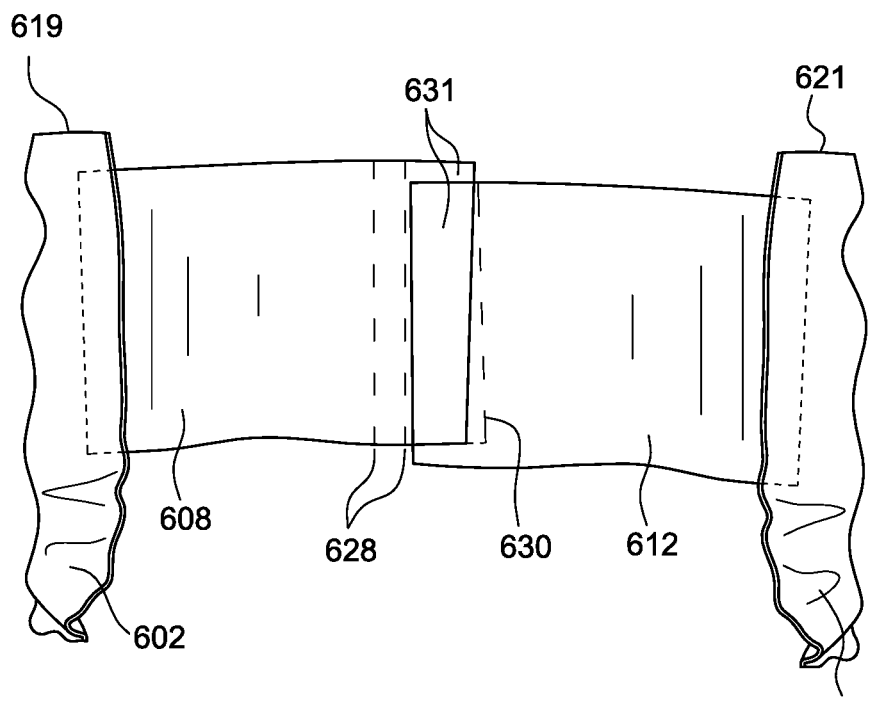
FIG. 11 is a plan view of the absorbent article of FIG. 10 in which the side panels have been rejoined.
Figure 12:
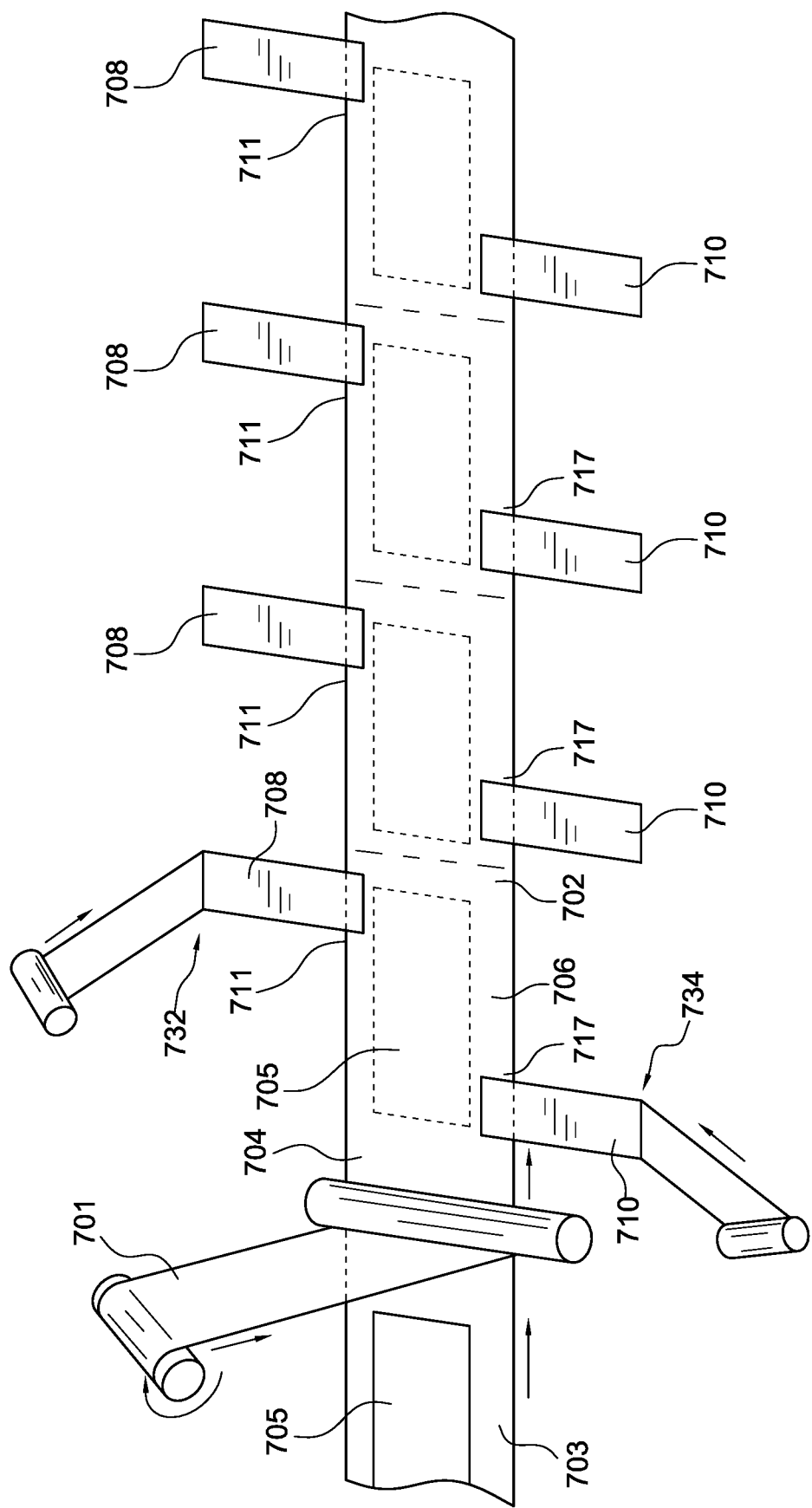
FIG. 12 is a representative diagram illustrating steps in an embodiment of a manufacturing process for manufacturing embodiments of an absorbent article.
Figure 13:
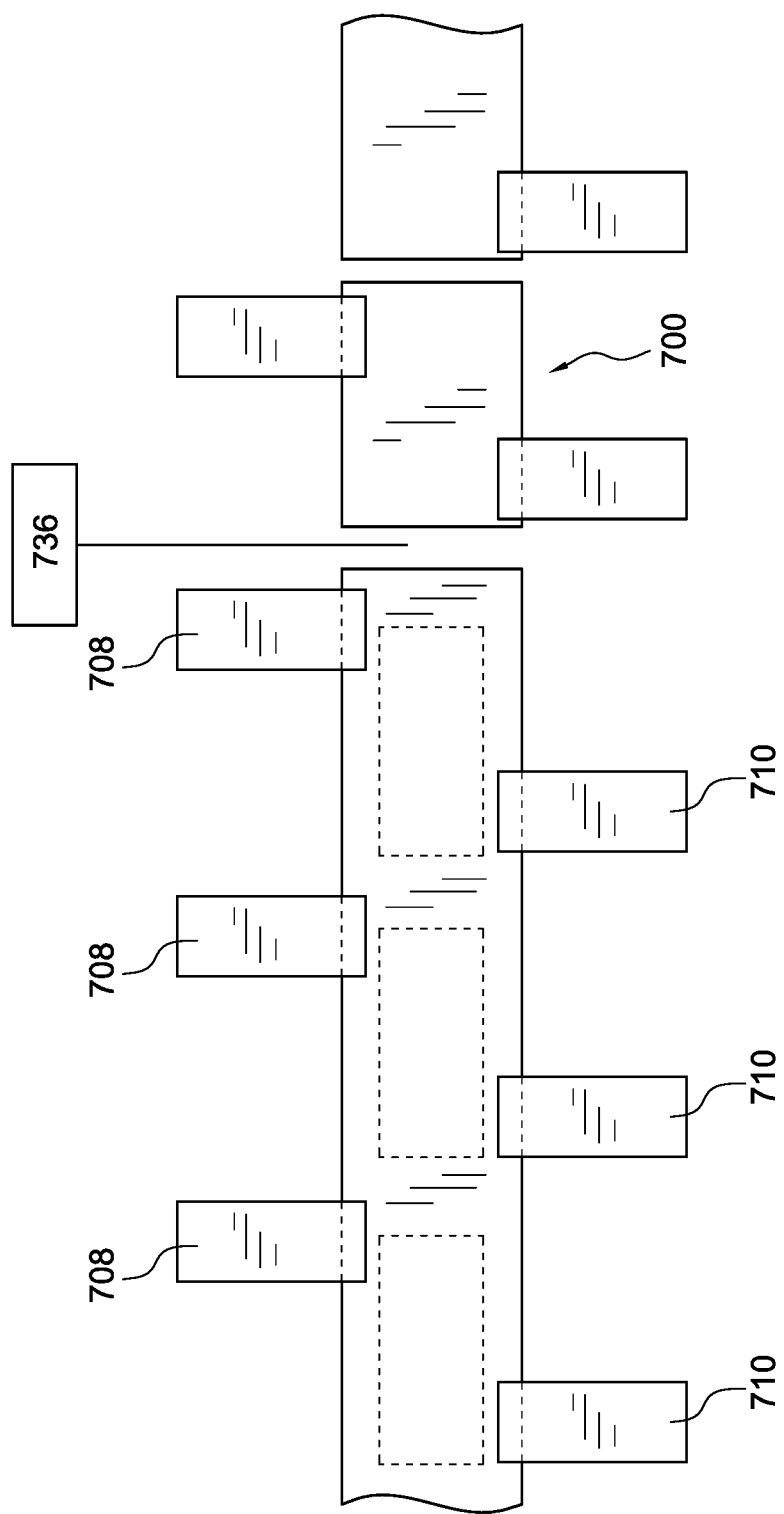
FIG. 13 is a representative diagram illustrating further steps in the embodiment of a manufacturing process of FIG. 12.
Figure 17:
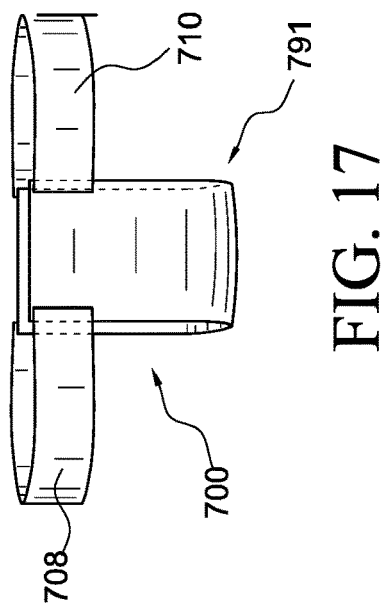
FIG. 17 is a perspective view of the embodiment of FIG. 15.
Figure 16:
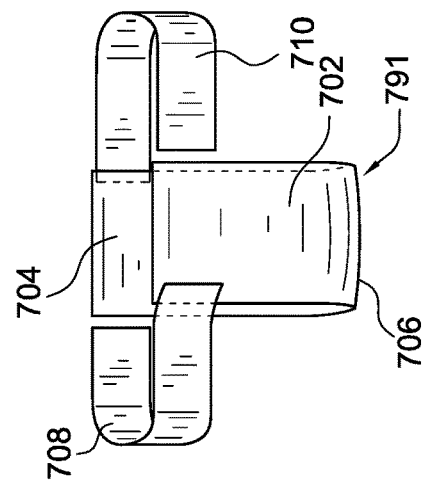
FIG. 16 is a perspective view of the embodiment of FIG. 14.
Figure 14:
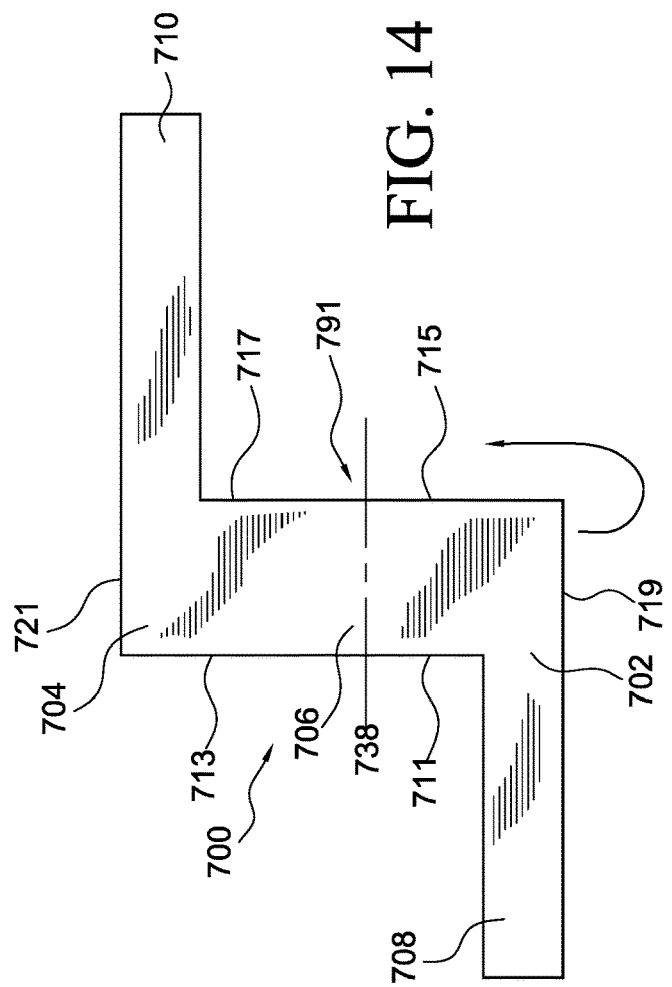
FIG. 14 is a plan view of an embodiment of an absorbent article in an open, flat condition.
Figure 15:
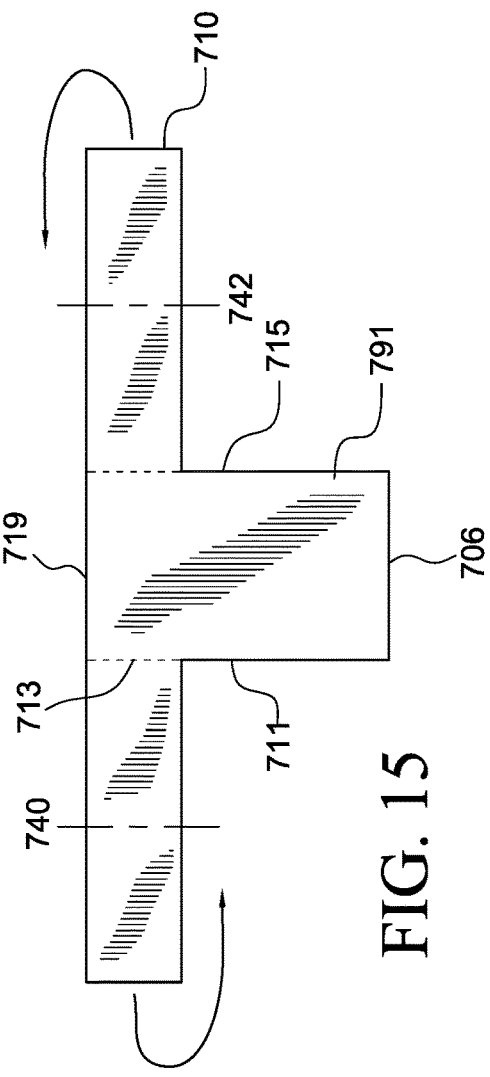
FIG. 15 is a plan view of a further embodiment of an absorbent article in an open, flat condition.

Cohesive materials may be pressure sensitive. In the embodiment illustrated in FIGS. 8-9, an absorbent article 500 comprises a front portion 502 and a rear portion 504. The absorbent article 500 comprises a front waist edge 519 on the front portion 502 and a rear waist edge 521 on a rear portion. A first side panel 508 is provided on a first side of the absorbent article, and a second side panel 510 is provided on a second side of the absorbent article. The first side panel 508 connects a first front side edge 511 with a first rear side edge 515. The second side panel 510 similarly connects a second front side edge 513 with a second rear side edge 517. The absorbent article 500 may comprise leg openings, which are defined by bottom edges 522. Once the article 500 is pulled over the hips of the wearer, the first and second side panels 508, 510 may be torn, and overlapped to refasten the side portions. For example, as illustrated in FIG. 10, once the side panels 508, 510 have been torn, instead of two side panels as initially provided, the absorbent article 600 now includes four side panels 608, 612, 610, 6H (right side panels not shown). The left side now includes first (front) and third side (rear) panels 608, 612 while the right side now includes second (front) and fourth (rear) side panels. These corresponding side panels may be overlapped at an attachment area 631 and rejoined as shown in FIG. 11, allowing the absorbent article to be re-donned or to be inspected and reconnected.

There are multiple benefits to having side portions constructed from cohesive materials. By way of example, firstly, by easily tearing the cohesive material first and second side portions 508, 510, the user can remove the absorbent article 500 without having to remove lower clothing from about the ankles and feet, for example when in a public restroom setting. Secondly, as cohesive material has a soft touch, the act of tearing the cohesive material will elicit minimal noise, thus helping the wearer to maintain dignity in public restroom settings. Thirdly, tearable cohesive material allows the wearer to customize the fit of the absorbent article 500 and achieve a more snug fit by overlapping segments of the side portions. Fourthly, since cohesive materials are self-adhering, they will not stick to clothing, hair or skin and consequently will not become a skin irritant or become soiled by intermittent contact with other surfaces, such as skin, hair or clothing.

Figure 7:
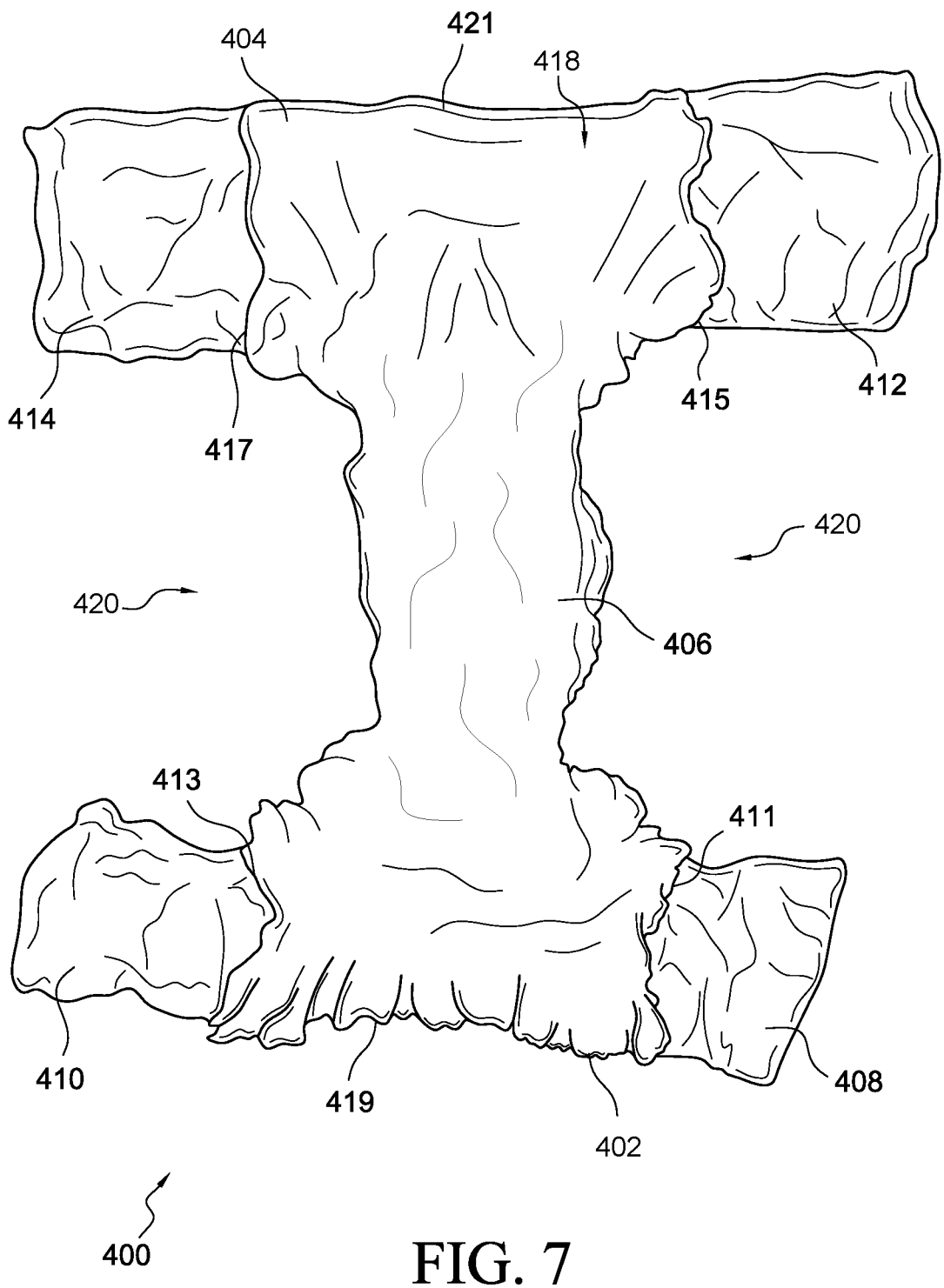
FIG. 7 is a plan view of an embodiment of an absorbent article in an open, flat condition.

In accordance with the embodiment of FIG. 7, the plurality of side panels may include four side panels 408, 410, 412, 414. The first side panel 408, joined to the left side front portion longitudinal edge 411; a second side panel 410, joined to the right side front portion longitudinal edge 413; a third side panel 412, joined to the left side rear portion longitudinal edge 415; and a fourth side panel 414, joined to the right side rear portion longitudinal edge 417.

To secure the side panels 408, 410, 412, 414 to form a waist opening 418 and leg openings 420, the cohesive material side panels 408, 410, 412, 414 are attached to one another such that first and third (front and rear) side panels 408, 412 join together and second and fourth (front and rear) side panels 410, 414 join together. The first and third 408, 412 and second and fourth 410, 414 side panels, respectively may overlap, or join inside face to inside face or outside face to outside face, or in any other technique suitable to cohesive joining cohesive material. Absorbent article 400 further comprises a crotch portion 406 extending between a front portion 402 and a rear portion 404. The front portion 402 comprises a front waist edge 419 and the rear portion 404 comprises a rear waist edge 421.

In accordance with the various embodiments, the absorbent article may include aesthetically pleasing color features so as to suggest that the article resembles the color features of traditional undergarments. By way of non-limiting example, the article may be buff colored, gray, or black, or include a multi-colored pattern, designs or indicia.

In accordance with the various embodiments, side panels constructed from a stretchable, cohesive material allows for a single article to fit a greater number size range of wearers. This reduces waste as there is a reduction in the amount of machinery needed to build multiple size accommodating articles, as well as less change over from product size to product size, thereby increasing efficiency in the manufacturing process.

Figure 8:
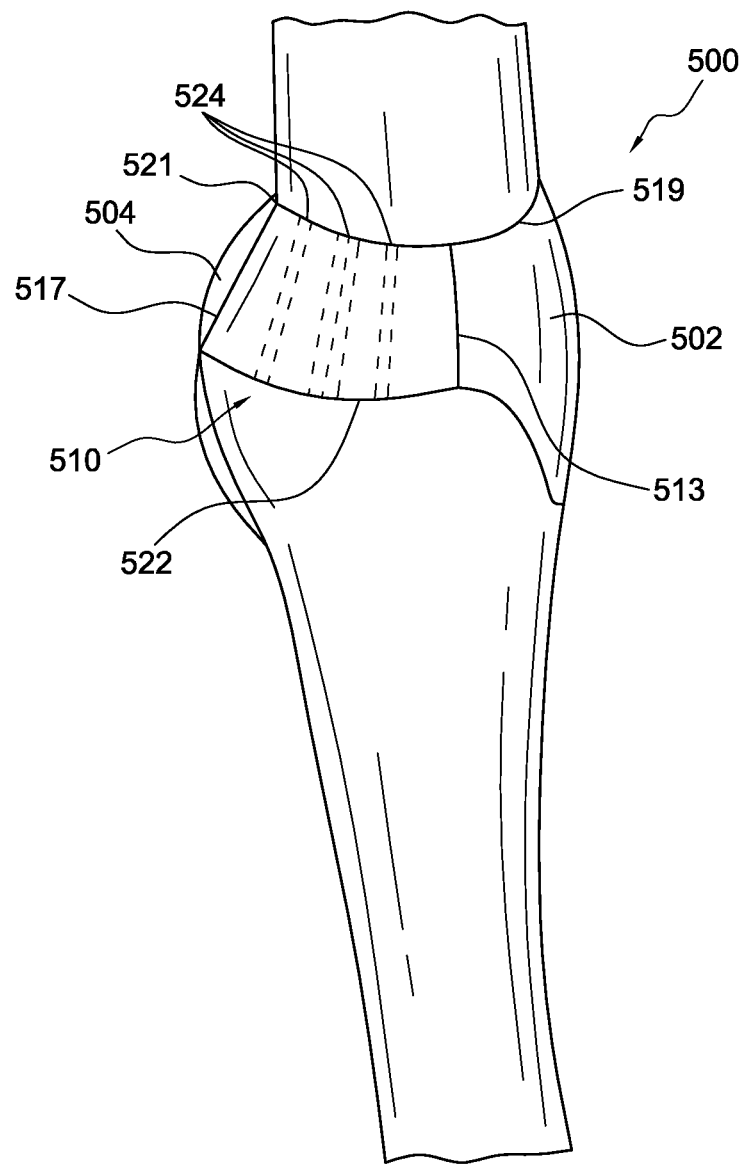
FIG. 8 is a side view of an embodiment of an absorbent article in a closed, use condition.

In an embodiment, the absorbent article may be customized to improve the fit around a wear's torso or to improve comfort. As illustrated in FIGS. 8 and 9, the side panels 508, 510 may include a sizing indicator 524. Non limiting sizing indicator 524 examples include lines, colors, symbols, graphics, letters, words, or other indicators. In another embodiment, the sizing indicator 524 may include frangible or perforated sections in the side portions 508, 510. In accordance with the various embodiments, sizing indicators can provide visual signals to a wearer offering suggested tear points 526 in the cohesive material.

In this way, after donning a brief style absorbent article 500, a wearer can adjust the fit of the absorbent article by tearing each of the first and second side panels 508, 510 at corresponding sizing indicator tear points 526. In use, a user tears side panel 508 along the sizing indicator tear points 526. Absorbent article 600 comprises a front portion 602 with a front waist edge 619 and a rear portion 604 comprises a rear waist edge 621. Instead of two side panels as initially provided, the absorbent article 600 now includes four side panels 608, 612 (right side panels not shown). The left side now includes first and third (front and rear) side panels 608, 612 while the right side now includes second and fourth (front and rear) side panels. In accordance with the embodiment of FIGS. 10-11, by tearing 630 the side panels 608, 610 at corresponding sizing indicator 624 positions, a symmetrical fit of the absorbent article 600 around the wearer's body will be maintained. In this way, the torn first and second side panels 608, 610 will extend laterally by substantially the same distance. Similarly, newly formed third and fourth side panels 612, 614 will extend laterally by substantially the same distance. Accordingly, when cohesively rejoining the first and third side panels 608, 612 and the second and fourth side panels, further sizing indicators 624 suggest zones for reattachment or landing 628. Maintaining symmetry of the absorbent article 600 around a wearer's body is critical to reducing sagging, bagging and leaking of an absorbent article 600 and ensuring a proper fit has been achieved.

In an alternative embodiment, a wearer may want to only tear one of the side panels, for example, following a surgical procedure to the wearer's waist or hip region. In accordance with this embodiment, the absorbent article is sized to extend up and over any surgical dressings. To improve the fit of the absorbent article, the wearer may only tear one side portion so as to reduce any sagging, bagging or leaking on the side opposite the surgical dressing. Said differently, the cohesive side panel extending over a surgical site is extensible over the surgical dressing on say, for example the left hip, but the right hip area does not include a surgical dressing, and thus the right side panel may be looser fitting. To improve the fit of the absorbent article relative to the right side, the wearer will tear the cohesive material side portion extending along the right side of the article, overlap the now torn side portions and improve the fit about the waist region. The untorn left cohesive material side panel does not include any raw edges or seams which could cause surgical site irritation.

While a brief style absorbent article is depicted, those skilled in the art will recognize that bikini, boxer, boxer brief and other styles of absorbent articles (for example, diapers and training pants) can be implemented without departing from the scope of the embodiments disclosed herein.

FIGS. 12-17 illustrate embodiments of a method for manufacturing an absorbent article 700 in accordance with the embodiments of FIGS. 3-6 and 8-11. Embodiments of the manufacturing method may include the following steps: (1) providing a layup for an absorbent article including a chassis 791 having a front portion 702, a rear portion 704 and a crotch portion 706 extending there between. The front portion 702 comprises a front waist edge 719 and the rear portion 704 comprises a rear waist edge 721. The absorbent article layup further includes providing a length of inner sheet 703 material and cut sections of absorbent and/or distribution layer 705 material in a first direction; (2) unwinding a continuous length of the outer sheet material 701 in a second direction; (3) providing a continuous length of side panel material in a third direction transverse to the first and second directions and cutting the side panel material into discreet lengths for placement along the front portion first longitudinal edge 711. This first cut piece of side portion material forms the first side panel 708 by feeding in a third direction, transverse to the first and second directions, a continuous length of side portion material through a slip and cut 732 (also known to those skilled in the art as cut and place) which can be performed with a cutting unit followed by a placing unit—as driven by either mechanical cam or servo motor unit, thereby providing an intermittent length of side portion material along a first side, first position of the absorbent article layup. The slip/cut applicator may also require a vacuum in order to hold the side portion within the unit until severed, accelerated and welded, bonded or adhered in place to the backsheet. In a fourth step, a second continuous length of side portion material is fed into the system in a fourth direction, different from the third direction and transverse to the first and second directions, a continuous length of side portion material through a slip and cut 734, thereby providing an intermittent length of second side panel 710 material along a second side longitudinal edge 717, second position of the absorbent article layup. In a fifth step, a cutoff and spacing unit 736 severs and spaces the layup into discreet absorbent articles 700. In a sixth step, a folding machine folds the absorbent article chassis 791 in half along an x axis 738; the front and rear portion waist portions 702, 704 are now aligned and left and right side panels 708, 710 extend along the x axis from their respective left side front portion 702 at 711 and right side rear portion 704 at 717. In a seventh step, the left side panel 708 is folded in half along they axis 740 and joined to the left side rear portion 713 by welding, bonding or adhering. Similarly, the right side panel 710 is folded in half along they axis 742 and joined to the right side front portion 715 by welding, bonding or adhering. The side panels 708, 710 may be affixed to either the inner layer 703 or the outer layer 701.

In an alternative embodiment, the side panels 708, 710 may be affixed between the inner layer 703 and outer layer 701.

While the present invention has been described with reference to one or more particular embodiments, those skilled in the art will recognize that many changes may be made thereto without departing from the spirit and scope of the present invention. Furthermore, components from one embodiment can be used in other non-exclusive embodiments. By way of example, any of the features of FIG. 3 described herein can include any of the features described in FIGS. 8-11. Similarly, each of the features of FIGS. 6-6A and 8-11 depict one side of an absorbent article. It is to be understood that an unillustrated second side of an absorbent article may be a mirror image of the embodiments of FIGS. 6-6A and 8-11 and thus will include each of the elements described herein. Each of these embodiments and obvious various thereof is contemplated as falling within the spirit and scope of the invention, which is set forth in the following alternative embodiments.

What is claimed is:

1. An absorbent article comprising:
   a chassis comprising an outer layer, an absorbent layer and an inner layer, the chassis further comprising:
      a first portion having a first side longitudinal edge and a second side longitudinal edge,
      a second portion having a first side longitudinal edge and a second side longitudinal edge, and
      a crotch portion extending between the first and second portions, wherein a portion of the chassis is configured to absorb fluids;
   a first side panel comprising a cohesive material, the first side panel extending transverse to the chassis first portion first side longitudinal edge from the first portion first side longitudinal edge to the chassis second portion first side longitudinal edge;
   a second side panel extending transverse to the chassis first portion second side longitudinal edge from the first portion second side longitudinal edge to the chassis second portion second side longitudinal edge,
   wherein the first and second side panels and first and second portions form a waist opening and first and second leg openings;
   wherein the first side panel comprising a single, integral panel of material in an initial configuration;
   wherein the first side panel is separable into a first side panel front part and a first side panel rear part in a subsequent configuration;
   wherein front and rear parts are reconnected by overlapping the front and rear parts at an attachment area; and
   wherein the cohesive material of the front part attaches to the cohesive material of the rear part in the attachment area without a secondary fastener.

2. The absorbent article of claim 1, wherein the first and second side panels are extensible.

3. The absorbent article of claim 1, wherein the first side panel front and rear parts are integrally formed in an initial state and are separable in a subsequent state by separating the front part from the rear part.

4. The absorbent article of claim 1, wherein the first side panel front and rear parts are integrally formed in an initial state and are separable in a subsequent state by tearing the front part from the second part.

5. The absorbent article of claim 4, wherein the first side panel further comprises a tear line.

6. The absorbent article of claim 5, wherein the tear line comprises a line of perforations.

7. The absorbent article of claim 6, wherein the tear line comprises a portion of the side panel having a lower tensile strength than a remainder of the side panel.

8. The absorbent article of claim 1, wherein the first side panel and the second side panel each comprise sizing indicators.

9. The absorbent article of claim 8, wherein the sizing indicator comprises a perforation.

10. The absorbent article of claim 8, wherein the sizing indicator comprises a visual indicia.

11. The absorbent article of claim 8, wherein the first side panel sizing indicator is complementary to the second side panel sizing indicator.

12. The absorbent article of claim 8, wherein the first side panel sizing indicator is substantially symmetrical to the second side panel sizing indicator.

13. The absorbent article of claim 1, wherein the sizing indicators comprise a tear point and a landing zone.

14. The absorbent article of claim 13, wherein when the first side panel is torn by hand substantially along the tear point the newly formed front and rear parts are cohesively reattached along the landing zone.

15. An absorbent article comprising:
a chassis comprising an outer layer, an absorbent layer and an inner layer, the chassis further comprising:
a first portion having a first side longitudinal edge and a second side longitudinal edge,
a second portion having a first side longitudinal edge and a second side longitudinal edge, and
a crotch portion extending between the first and second portions, wherein a portion of the chassis is configured to absorb fluids;
a side panel extending transverse to the chassis first portion first side longitudinal edge and from the first portion first side longitudinal edge to the chassis second portion first side longitudinal edge, the side panel comprising a single, integral panel of material having a front part and a rear part in an initial configuration;
wherein the side panel front part and a rear part are separated by severing the front part from the rear part in a subsequent configuration; and
wherein the front and rear parts are reconnected by overlapping the front and rear parts at an attachment area in a further subsequent configuration.

16. The absorbent article of claim 15, wherein the side panel comprises a cohesive material.

17. The absorbent article of claim 16, wherein the front part and rear part are connected by engagement of the cohesive material of the front part with the cohesive material of the rear part without use of a secondary fastener.

* * * * *